United States Patent [19]

Lindstrom

[11] Patent Number: 4,715,858
[45] Date of Patent: Dec. 29, 1987

[54] EPICORNEAL LENS

[76] Inventor: Richard L. Lindstrom, 1065 W. Ferndale Rd., Wayzata, Minn. 55391

[21] Appl. No.: 889,174

[22] Filed: Jul. 25, 1986

[51] Int. Cl.$^4$ .............................................. A61F 2/14
[52] U.S. Cl. ...................................... 623/5; 128/1 R; 128/305; 427/2
[58] Field of Search ........................................ 623/4-6, 623/66; 128/1 R, DIG. 21, 303 R, 305; 427/2

[56] References Cited

U.S. PATENT DOCUMENTS

| | | | |
|---|---|---|---|
| 2,714,721 | 8/1955 | Stone, Jr. ................................. | 623/5 |
| 2,952,023 | 9/1960 | Rosen ..................................... | 623/4 |
| 3,992,563 | 11/1976 | Tanaka .................................... | 623/4 |
| 4,189,546 | 2/1980 | Deichert et al. ....... | 128/DIG. 21 X |
| 4,589,881 | 5/1986 | Pierschbacher et al. ...... | 128/1 R X |
| 4,624,669 | 11/1986 | Grendahl ......................... | 128/1 R X |

FOREIGN PATENT DOCUMENTS 2705234  8/1978  Fed. Rep. of Germany .......... 623/5

Primary Examiner—Ronald L. Frinks
Attorney, Agent, or Firm—Hugh D. Jaeger

[57] ABSTRACT

A synthetic epicorneal lens for use in the treatment of refractive errors. The lens is of a plastic that is compatible with the cornea, may be gas permeable or metabolite permeable, and may be coated with a basement membrane material such as fibronectin or laminen. The lens can be made from polymers, hydrogel, silicone, fluoropolymer, cellulose acetate butyrate, or other like material.

13 Claims, 7 Drawing Figures

EPICORNEAL LENS

BACKGROUND OF THE INVENTION

The present invention relates to a lens for the eye, and more particularly, pertains to a synthetic epicorneal lens which may be coated with a basement membrane material.

DESCRIPTION OF THE PRIOR ART

The prior art lenses have been tissue lenses which have not been entirely successful, nor entirely acceptable in the ophthalmology field. Synthetic lenses per se have not been pursued based on the limitations of prior art technology which is now being advanced.

The present invention overcomes the disadvantages of the prior art by providing a synthetic epicorneal lens which may be coated with a basement membrane material.

SUMMARY OF THE INVENTION

The general purpose of the present invention is to provide a synthetic epicorneal lens which may be coated with a basement like material. This allows for growth of the epithelium over the synthetic coated lens.

According to one embodiment of the present invention, there is provided a synthetic epicorneal lens of a bio-compatible material which may be coated with a basement like material to enhance growth of epithelium over the lens. The material can be fibronectin or laminen.

DESCRIPTION OF THE PREFERRED EMBODIMENTS

Figure 1:
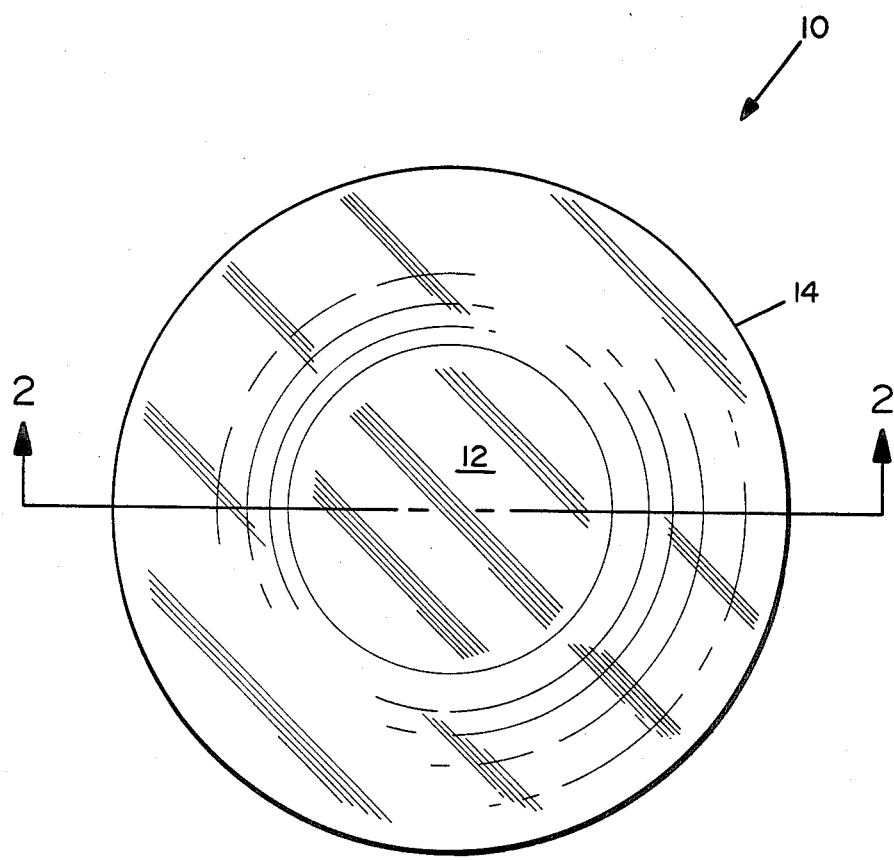
FIG. 1 illustrates a top view of a synthetic epicorneal lens with a top coating for enhancing growth of the epithelum.

FIG. 1 illustrates a top view of a synthetic epicorneal lens 10 where the lens is of a synthetic bio-compatible material. Such materials include polymers, hydrogel, silicone, fluoropolymer, cellulose acetate butynate, or other like materials which are gas permeable or metabolite permeable. The lens is provided with a radius of curvature to provide for appropriate conformance to the cornea, or in the alternative, for providing support and shaping of the cornea for correcting the specific refractive condition which includes aphakia, myopia, and keratoconus. The lens optic conforms to the top surface of the stroma and tapers to the edge 14 for accommodation in a surgical slit as described in FIG. 3. The lens also includes an optic shape as illustrated dependent upon the particular circumstances of implant. The specific thickness as well as curvature of the lens optic 12 is determined for the particular epikeratophakia condition which determines the thickness of the lens, the curvature of the lens as well as the specific edge structure 14 of the lens. A basement membrane material such as fibronectin or laminen is coated over the lens, and provides for growth of the epithelium over the top surface of the lens.

Figure 2:
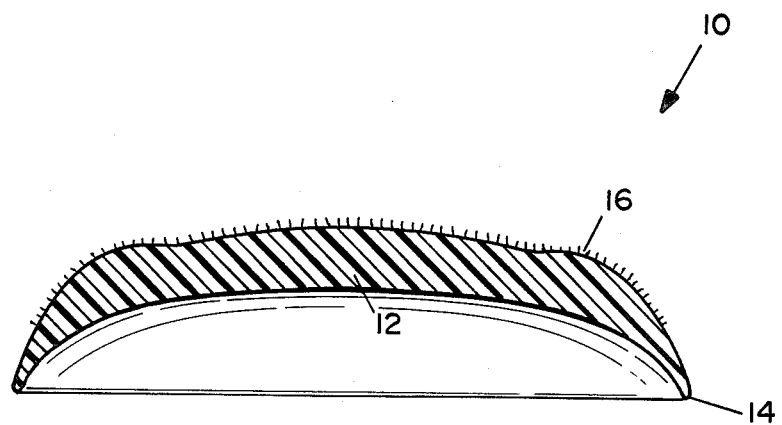
FIG. 2 illustrates a view taken along line 2—2 of FIG. 1.

FIG. 2 illustrates a side view of the lens 10 where all numerals correspond to those numerals previously described. Particularly illustrated is the basement membrane 16 material coating the top surface of the lens as well as about the edge of the lens. It is only necessary to provide a minimal coating over the area where the epithilium is to grow over the top surface of the lens optic, but it may also be desirable to coat a larger area of the lens optic as so desired. The coating provides that the epithelium grows over and adheres to the surface of the lens optic. The growth of the epithelium is either through the nature of material or through the coating over the lens optic such as by the basement membrane material. The lens optic 12 is configured as previously discussed to be accommodated in the cornea and as later described in detail. The edge 14 tapers for purposes of accommodation in a tight seal in the cornea.

MODE OF OPERATION

Figure 3A:
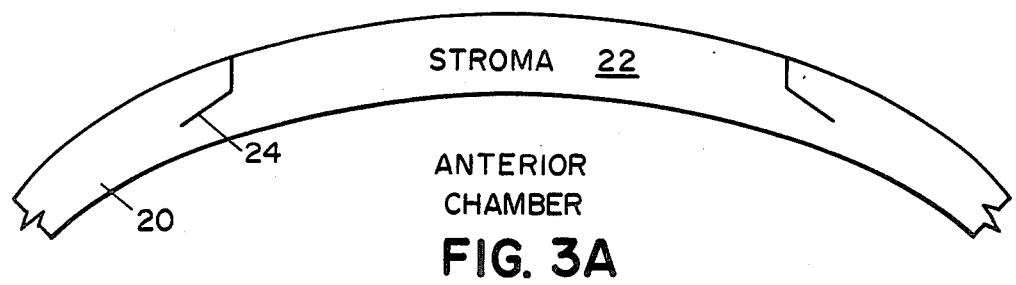
FIG. 3A is a cross-section of a cornea with the epithelium removed, and bearing a trefine incision in the stroma.
Figure 3B:
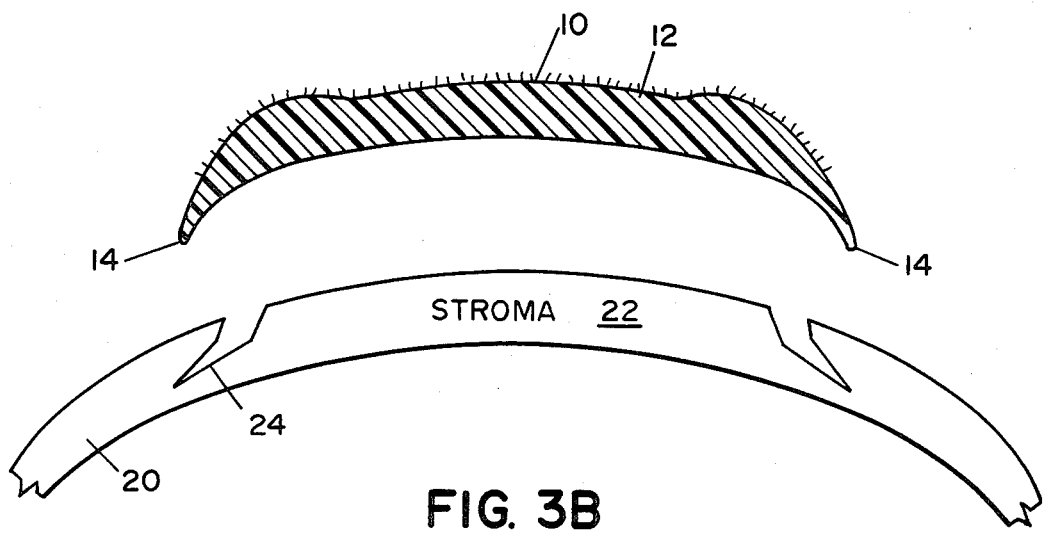
FIG. 3B is a cross-section of the cornea of FIG. 3A showing undermining of the incision.
Figure 3C:
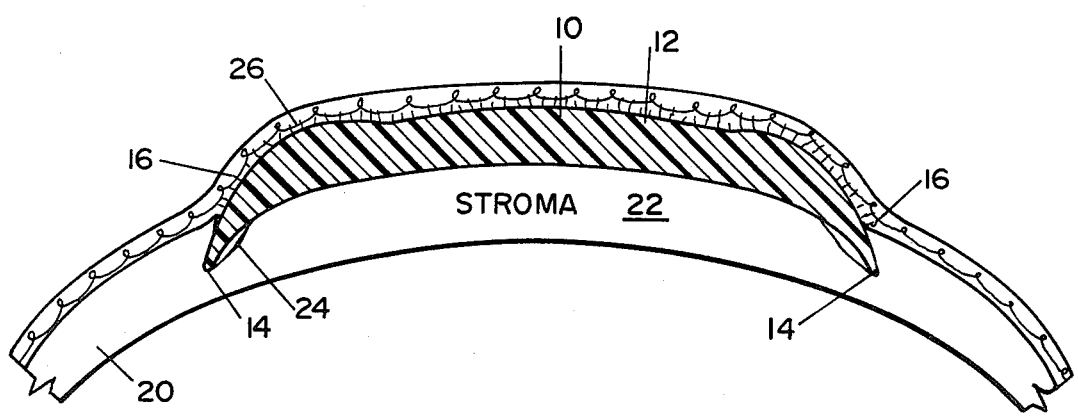
FIG. 3C is a cross-section of the cornea of FIG. 3B showing the lens implanted on the cornea.

FIGS. 3A-3C illustrates the surgical technique for implanting the lens is that used in the technique of epikeratophakia which includes removing the epithelium, creating the annular keratotomy, and either suturing or gluing the lens in place as illustrated in the figures.

FIG. 3A illustrates a cross section of the cornea 20 with the epithelum removed and a trefine incision 24 made into the stroma of the cornea.

FIG. 3B illustrates the undermining of the incision.

FIG. 3C illustrates the lens 10 applied over the cornea 20 about the stroma 22, and the edge 14 is inserted into the incision 24 providing a tight seal about the continuous ring through the use of surgical biocompatible broadbase adhesive. The particular geometrical structure of the lens optic 12 is determined by the desired correction in the eye. Subsequently, the membrane material provides for and enhances growth of the epithelium 26 over the lens optic 12. The placement of the lens is on top of the stroma and under the epithelium.

ALTERNATIVE EMBODIMENTS

Figure 4:
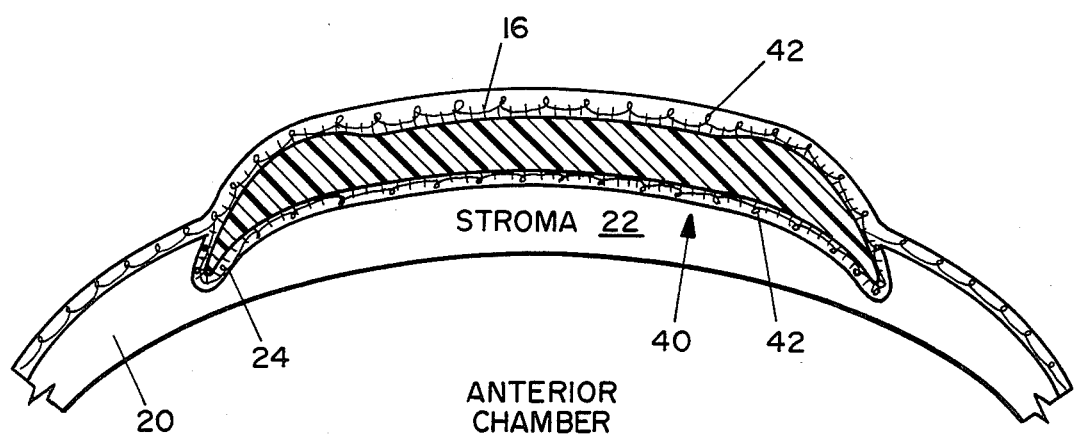
FIG. 4 illustrates a cross section of an alternative embodiment of a coated epicorneal lens; and, FIG. 5 illustrates a cross section of a epithelium lens of FIGS. 1-3 including a plurality of holes.

FIG. 4 illustrates a cross section of an alternative embodiment of an epicorneal lens 40 where both the upper and lower surfaces of the lens are coated with basement membrane material 42 so that growth of the epithelium is provided on both sides of the lens 10.

Figure 5:
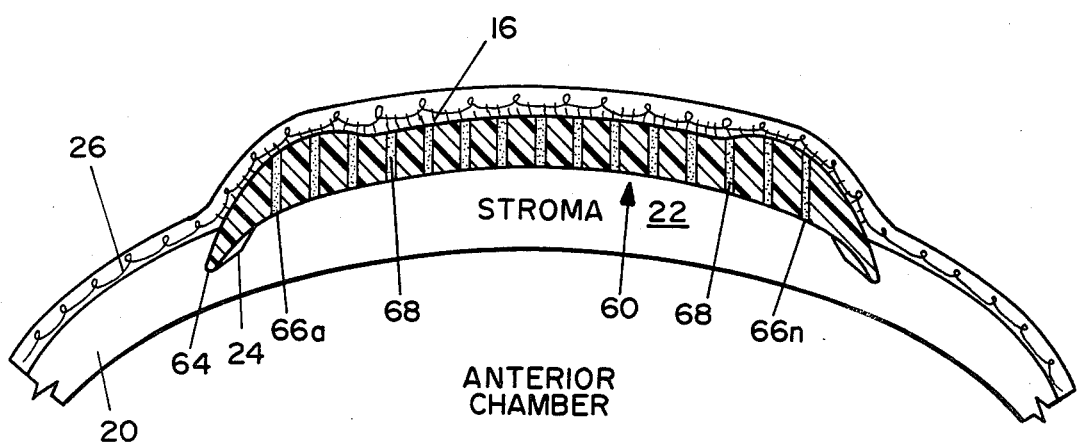

FIG. 5 illustrates a cross section of another alternative embodiment of an epicorneal lens 60 including a lens optic 62, an edge 64 formed by the surfaces of the optic, and a plurality of holes 66a–66n throughout the optic. The holes can also be filled with either a gas permeable material or polymer silicone, hydrogel, CAB, a metabolite permeable material, a biocompatible polymer, a biocompatible material, or a neutral or negatively charged material. The substance of the material in the holes is denoted as 68. The holes provide for the passage of nutrients, fluids, and gases between the stroma and the epithilium.

Various modifications can be made to the present invention without departing from the apparent scope thereof.

I claim:
1. Synthetic epicorneal lens comprising:
   a. lens optic of a bio-compatible material which is gas permeable or metabolite permeable; and,
   b. coating of a basement membrane over the entire upper surface of said lens for enhancing epithelium growth.
2. Lens of claim 1 wherein said lens is made of silicone.
3. Lens of claim 1 wherein said lens is made of hydrogel.
4. Lens of claim 1 wherein said lens is made of a polymer.
5. Lens of claim 1 wherein said basement membrane material is fibronectin.
6. Lens of claim 1 wherein said basement membrane material is laminen.
7. Lens of claim 1 wherein said bottom surface is coated with said basement membrane.
8. Lens of claim 1 wherein said lens is provided with a plurality of holes.
9. Lens of claim 8 wherein said holes are filled with a material.
10. Epicorneal lens comprising:
    a. lens optic means having upper and lower surfaces for implant in an eye between a stroma and epithilium of the eye;
    b. said lens optic means of a synthetic biocompatible material; and,
    c. a basement membrane material completely coating at least one of said surfaces of said lens optic means with a material for enhancing epithelium growth.
11. Lens of claim 10 wherein said material is laminen.
12. Lens of claim 10 wherein said material is fibronectin.
13. Lens of claim 10 wherein said lens optic means includes a plurality of fenestrations.

* * * * *